United States Patent [19]

Tsubakimoto et al.

[11] Patent Number: 4,666,983

[45] Date of Patent: May 19, 1987

[54] ABSORBENT ARTICLE

[75] Inventors: Tsuneo Tsubakimoto; Tadao Shimomura, both of Toyonaka; Yoshio Irie, Nishinomiya, all of Japan

[73] Assignee: Nippon Shokubai Kagaku Kogyo Co., Ltd., Osaka, Japan

[21] Appl. No.: 486,318

[22] Filed: Apr. 19, 1983

[30] Foreign Application Priority Data

Apr. 19, 1982 [JP] Japan ................................ 57-63905

[51] Int. Cl.[4] .............................................. C08F 8/32
[52] U.S. Cl. .................................... 525/119; 525/123; 525/329.7; 525/329.9; 525/375; 525/381; 525/382; 525/384; 527/314
[58] Field of Search ................. 525/329.7, 329.9, 119, 525/123; 527/314

[56] References Cited

U.S. PATENT DOCUMENTS 3,966,679  6/1976  Gross ............................... 525/327.6
4,270,977  6/1981  Herman et al. ........................ 524/35
4,320,040  3/1982  Fujita et al. .......................... 524/459
4,340,706  7/1982  Obayashi et al. ..................... 526/240
4,446,261  5/1984  Yamasaki et al. .................... 524/502

FOREIGN PATENT DOCUMENTS 55-84304    6/1980  Japan .
55-131608  10/1981  Japan .

Primary Examiner—Joseph L. Schofer
Assistant Examiner—Bernard Lipman
Attorney, Agent, or Firm—Sherman and Shalloway

[57] ABSTRACT

An absorbent article obtained by mixing 100 parts by weight of an absorbent resin powder having a carboxyl group with 0.001 to 10 parts by weight of a crosslinking agent having at least two functional groups capable of reacting with the carboxyl group per molecule and reacting the absorbent resin powder with the crosslinking agent to crosslink the molecular chains existing at least in the vicinity of the surface of the absorbent resin powder.

26 Claims, No Drawings

ABSORBENT ARTICLE

This invention relates to an absorbent article. More specifically, it relates to an absorbent article which, when in contact with an aqueous fluid, absorbs it to a great extent, and has a high ability to hold water even under pressure.

Attempts have previously been made to use absorbent resins as one component material of sanitary products for absorbing body fluids, such as sanitary napkins and paper diapers. These absorbent resins include, for example, a hydrolyzate of a starch/acrylonitrile graft copolymer, a neutralization product of a starch/acrylic acid graft copolymer, a saponification product of a vinyl acetate/an acrylate ester copolymer, a hydrolyzate of an acrylonitrile copolymer, a hydrolyzate of an acrylamide copolymer, crosslinked products of the foregoing copolymers, self-crosslinkable poly(sodium acrylate) obtained by inverse phase suspension polymerization, and a crosslinked product of a partial neutralization product of polyacrylic acid.

These conventional absorbent resins all have the serious defect that their rates of absorption are lower than fluff pulp and paper. For example, when urine is excreted on a paper diaper having such a conventional absorbent resin incorporated therein, urine remains in touch with the skin for some time and makes the wearer uncomfortable. This is because of the small amount of urine which the diaper can absorb, and it takes time before the diaper has a dry touch. Various attempts have therefore been made to increase the surface area of the resin by decreasing its particle size or converting it into granules or flakes. When the particle size of the absorbent resin is decreased, it generally forms "fisheyes" upon contact with urine, and this retards the speed of urine absorption. When the absorbent resin is molded into granules, each of the granules constitutes a "fish-eye" and the speed of absorption becomes slower. The use of flaky absorbent resin increases the speed of absorption to some extent, but not sufficiently. Also, the amount of absorption at equilibrium by the flaky resin is small because the resin generally has a low molecular weight so as to make the flake-forming operation easy. Furthermore, flaky resins are necessarily bulky and require large facilities for transportation and storage. This is not economically advantageous.

It is an object of this invention therefore to provide an absorbent having a high speed of absorption and a large amount of absorption at equilibrium.

The present inventors have made extensive investigations, and found that an absorbent article meeting the above object can be obtained by mixing an absorbent resin powder having a carboxyl group with a crosslinking agent having a least two functional groups capable of reacting with the carboxyl group, and reacting the mixture (optionally under heat) to crosslink the molecular chains existing at least in the vicinity of the surface of the powder.

The absorbent resin which is used in this invention should have a carboxyl group. It may be at least one resin selected, for example, from a hydrolyzate of a starch/acrylonitrile graft copolymer, a partial neutralization product of a starch/acrylic acid graft copolymer, saponification products of vinyl acetate/acrylic ester copolymers, hydrolyzates of acrylonitrile copolymers, hydrolyzates of acrylamide copolymers, crosslinked products of the foregoing copolymers, a partial neutralization product of polyacrylic acid, and a crosslinked partial neutralization product of polyacryllic acid. Those having a crosslinked structure are suitable.

Preferred absorbent resins for use in this invention are shown in (1) to (5) below.

(1) Alkali metal acrylate-type polymers obtained by copolymerizing 100 parts by weight of an acrylate salt type monomer consisting of 1 to 50 mole% of acrylic acid and 50 to 99 mole% of an alkali metal acrylate and 0 to 5 parts by weight of a crosslinkable monomer in aqueous solution in a monomer concentration of at least 20% by weight, and drying the resulting gel-like hydrous polymer by heating.

(2) Absorbent resins obtained by dispersing an aqueous solution of acrylic acid and/or an alkali metal acrylate containing a water-soluble radical polymerization initiator and as required, a crosslinkable monomer in an alicyclic and/or an aliphatic hydrocarbon solvent in the presence of a surface-active agent having an HLB of 3 to 12, and subjecting the mixture to suspension polymerization.

(3) Saponification products of copolymers of vinyl esters and ethylenically unsaturated carboxylic acids or their derivatives.

(4) Absorbent resins obtained by polymerizing in an aqueous medium starch and/or cellulose, a monomer having a carboxyl group or capable of forming a carboxyl group upon hydrolysis, and if required, a crosslinking monomer, and as required, hydrolyzing the resulting polymer.

(5) Absorbent resins obtained by reacting an alkaline substance with a maleic anhydride-type copolymer composed of maleic anhydride and at least one monomer selected from α-olefins and vinyl compounds, and as required, reacting the reaction product with a polyepoxy compound.

There is no particular limitation on the amount of carboxyl groups which the absorbent resin should have. Preferably, at least 0.01 equivalent of carboxyl groups are present per 100 g of the absorbent resin. In the case of a partial neutralization product of polyacrylic acid for example, the proportion of the non-neutralized portion is preferably 1 to 50 mole%.

There is no particular restriction on the particle shape of the absorbent resin used in this invention. The absorbent resin may be in the form of spheres obtained by inverse phase suspension polymerization, flakes obtained by drum drying, or irregularly shaped particles obtained by pulverizing the resin mass. From the standpoint of the speed of absorption, the particles of the absorbent resin are preferably small. Preferably, the proportion of those particles which pass through a 60-mesh sieve is at least 70% by weight. If this proportion is less than 70% by weight, the speed of absorption tends to decrease.

The crosslinking agent used in this invention should have per molecule at least two functional groups capable of reacting with the carboxyl group.

Examples of such a crosslinking agent include polyhydric alcohol compounds, polyglycidyl ether compounds, polyfunctional aziridine compounds, polyfunctional amine compounds and polyfunctional isocyanate compounds. The polyhydric alcohol compounds are especially suitable.

Specific examples of the polyhydric alcohol compounds are diethylene glycol, triethylene glycol, polyethylene glycol, glycerol, polyglycerol, propylene glycol, diethanolamine, triethanolamine, polyoxy propylene, oxyethylene/oxypropylene block copolymer, sorbitan fatty acid esters, polyoxyethylene sorbitan fatty acid esters, trimethylolpropane, pentaerythritol and sorbitol.

Specific examples of the polyglycidyl ether compounds are ethylene glycol diglycidyl ether, and glycerin diglycidyl ether.

Specific examples of the polyfunctional aziridine compounds are Chemitite PZ-33: a tradename for 2,2-bishydroxymethylbutanol-tris[3-(1-aziridinyl)propionate], Chemitite HZ-22: 1,6-hexamethylenediethyleneurea and Chemitite DZ-22: diphenylmethanebis-4,4'-N,N'-diethyloneurea, all of which are manufactured by Nippon Shokubai Kagaku Kogyo Co., Ltd.

Specific examples of the polyfunctional amines are ethylenediamine, triethylenetetramine, tetraethylenepentamine, pentaethylenehexamine, and polyethylenimine.

Specific examples of the polyfunctional isocyanate compounds are 2,4-tolylene diisocyanate and hexamethylene diisocyanate.

The amount of the crosslinking agent used in this invention differs depending upon the kind of the absorbent article. Generally, it is 0.001 to 10 parts by weight per 100 parts by weight of the adsorbent resin. When it exceeds 10 parts by weight, the resin is too highly crosslinked, and the resulting product has a low ratio of absorption. On the other hand, when it is less than 0.001 part by weight, there is no effect of using the crosslinking agent.

In the present invention, the absorbent resin powder and the crosslinking resin are mixed by ordinary mixers such as a V-shaped rotating mixer, a ribbon mixer, a screw mixer, a rotating disc mixer and a fluidized bed mixer.

The reaction between the carboxyl groups of the absorbent resin powder and the crosslinking agent may take place at room temperature as in the case of using an aziridine compound as the crosslinking agent. To promote the reaction, however, it is usually preferred to perform heat-treatment. The heat-treatment temperature differs depending upon the kind of the crosslinking agent. Usually, it is 90° to 300° C., preferably 120° to 250° C., for the polyhydric alcohols, 50° to 300° C., preferably 90° to 250° C., for the polyglycidyl ether compounds, 10° to 300° C., preferably 20° to 250° C., for the polyfunctional aziridine compounds, 90° to 300° C., preferably 120° to 250° C., for the polyfunctional amine compounds, and 10° to 300° C., preferably 20° to 250° C., for the polyfunctional isocyanate compounds.

Ordinary dryers or heating ovens can be used for heat-treating a mixture of the absorbent resin powder and the crosslinking agent. They include, for example, an agitated trough dryer, a rotating dryer, a rotating disc dryer, a kneading dryer, a fluidized bed dryer, a pneumatic conveying dryer, and an infrared dryer.

In the mixing and heat-treatment, the mixer may be used to perform mixing and heat-treatment simultaneously if the mixer is of a type that can be heated. Or mixing and heat-treatment may be carried out simultaneously in the heat-treating machine if the heat-treating machine is of a type which permits stirring.

The absorbent article of this invention obtained in the above manner has various advantages over the known conventional absorbent resins. The absorbent article of this invention can be produced at a low cost by an industrially simple method which involves mixing the absorbent resin with the crosslinking agent and reacting them with each other. Since it is less susceptible to fish-eye formation than the known conventional absorbent resins, it has a high speed of absorption. Furthermore, the absorbent resin in accordance with this invention is difficult of caking upon moisture absorption.

The absorbent article of this invention can be used as an absorbent for paper diapers, sanitary napkins, etc. and can find other wide applications as, for example, a flocculating agent for sludges, a dew formation inhibitor for building materials, a water holding agent for agriculture and horticulture, and a drying agent.

The following examples illustrate the present invention specifically. It should be understood that the scope of this invention is not to be limited to these examples alone. Unless otherwise specified, the percentages and parts in these examples are by weight.

EXAMPLE 1

Four thousand parts of a 43% aqueous solution of an acrylic acid salt-type monomer composed of 74.95 mole% of sodium acrylate, 25 mole% of acrylic acid and 0.05 mole% of trimethylolpropane triacrylate was polymerized in the presence of 0.6 part of ammonium persulfate as a polymerization catalyst and 0.2 part of sodium hydrogen sulfite as a promoter under a nitrogen atmosphere at 55° to 80° C. The resulting gel-like hydrous polymer was dried in a hot air dryer at 180° C., and pulverized by a vibratory pulverizer to obtain particles which passed through a 100-mesh sieve (powder A) and particles which passed through a 60-mesh sieve (powder B).

Glycerol (0.3 part) was added to 100 parts of powder A, and they were mixed by a screw mixer. The mixture was heat-treated by a rotating disc dryer. Specifically, the mixture was placed in a thickness of 1 cm on a disc heated with a heat medium at 220° C., and heated for 15 minutes while it was agitated by a scraper. Thus, an absorbent (1) was obtained. Powder (B) was heat-treated in the same way to obtain an absorbent (2). At the end of the 15-minute heating, both of these absorbents had a temperature of 210° C.

0.2 g of each of these absorbents was put uniformly in teabag-type bags (40 mm×150 mm), and dipped in 0.9% salt solution. Thirty seconds later and 10 minutes later, the weight of the absorbent was measured. The ratio of absorption of the absorbent was calculated in accordance with the following equation using the absorbed weight of a teabag-type bag alone as a blank.

$$\text{Ratio of absorption} = \frac{\text{Weight after absorption (g)} - \text{Blank (g)}}{\text{Weight of the powder (g)}}$$

The presence or absence of fish-eyes was determined by dropping a small amount of the absorbent on a sheet of paper wetted with water, and observing the state of the absorbent.

The results are shown in Table 1. Table 1 shows that the rates of absorption of the absorbents (1) and (2) are markedly improved as compared with powders A and B.

EXAMPLE 2

Absorbents (3) to (10) were produced in the same way as in Example 1 except that the following polyhydric alcohols were respectively added to powder A instead of glycerol.

Polyethylene glycol (average molecular weight 300) [for absorbent (3)],
polyethylene glycol (average molecular weight 400) [for absorbent (4)],
polyethylene glycol (average molecular weight 600) [for absorbent (5)],
triethanolamine [for absorbent (6)],
sorbitan monolaurate [for absorbent (7)],
polyoxyethylene sorbitan monostearate [for absorbent (8)],
trimethylolpropane [for absorbent (9)], and
sorbitol [for absorbent (10)].

At the end of the heat-treatment for 15 minutes, all of these absorbents had a temperature of 210° C.

The properties of the absorbents (3) to (10) were evaluated in the same way as in Example 1. The results are shown in Table 1.

EXAMPLE 3

A reaction vessel equipped with a stirring rod, a nitrogen blowing tube and a thermometer was charged with 50 parts of corn starch, 200 parts of water and 1000 parts of methanol, and they were stirred at 50° C. for 1 hour under a nitrogen stream. The mixture was cooled to 30° C. Then, 25 parts of acrylic acid, 75 parts of sodium acrylate, 0.5 part of methylenebis-acrylamide, 0.1 part of ammonium persulfate as a polymerization catalyst and 0.1 part of sodium hydrogen sulfite as a promoter were added. They were reacted at 60° C. for 4 hours to form a white suspension.

The white suspension was filtered, and the resulting powder was washed with a 2:10 by weight water-methanol mixture. It was dried at 60° C. under reduced pressure for 3 hours, pulverized, and sieved on a 100 mesh wire gauze to obtain particles which passed through it (powder C).

One part of glycerol was added to 100 parts of powder C, and they were mixed in a rotating disc mixer. The resulting mixture was heat-treated for 10 minutes with hot air at 200° C. in a fluidized bed dryer to obtain an absorbent (11). When it was taken out from the dryer it had a temperature of 180° C. The properties of the absorbent (11) were evaluated in the same way as in Example 1. The results are shown in Table 1.

EXAMPLE 4

Benzoyl peroxide (0.8 part) was added as a polymerization initiator to a mixture of 60 parts of vinyl acetate and 40 parts of methyl acrylate. The mixture was dispersed in 300 parts of water containing 3 parts of partially saponified polyvinyl alcohol and 10 parts of sodium chloride. The dispersion was subjected to suspension polymerization at 65° C. for 6 hours. The polymerization product was filtered and dried to give a copolymer. The copolymer was saponified, washed, dried, pulverized and sieved to give particles which passed through a 60-mesh sieve (powder D).

One part of trimethylolpropane was added to 100 parts of powder D. The mixture was put in a ribbon blender whose jacket was heated at 230° C. with a heat medium, and worked for 15 minutes to perform both mixing and heat-treatment to give an absorbent (12). At the end of the 15-minute heat-treatment, the absorbent (12) had a temperature of 210° C. The properties of the absorbent (12) were evaluated in the same way as in Example 1. The results are shown in Table 1.

EXAMPLE 5

A reactor was charged with 300 parts of n-hexane, and 0.7 part of sorbitan monostearate was dissolved in it. An aqueous monomer solution obtained by dissolving 30 parts of acrylic acid in 40 parts of water, neutralizing the solution with 12.5 parts of sodium hydroxide, and further dissolving 0.05 part of potassium persulfate in it was dispersed in the resulting solution and polymerized at 65° C. for 5 hours under a nitrogen stream. After the polymerization, the product was dried under reduced pressure to form a powder (E).

One part of polyethylene glycol 300 was added to 100 parts of powder E, and they were mixed in a V-shaped mixer. The resulting mixture was placed thinly on a belt conveyor and passed through an infrared dryer to heat-treat it and give an adsorbent (13). The average heating time was 4 minutes, and at the exit of the dryer, the absorbent (13) had a temperature of 230° C.

The properties of the absorbent (13) were evaluated in the same way as in Example 1. The results are shown in Table 1.

EXAMPLE 6

154 parts of isobutylene/maleic anhydride copolymer, 64 parts of sodium hydroxide and 398 parts of water were mixed, and heated with stirring at 90° C. for 2 hours to prepare a uniform aqueous solution. Then, 2.5 parts of glycerol diglycidyl ether was added to the aqueous solution, and after mixing, the mixture was poured into a vat. The vat was placed in a hot air oven at 110° C. to induce crosslinking reaction. The product was dried, pulverized and sieved to give particles which passed through a 60-mesh sieve (powder F).

One hundred parts of powder F and 0.5 part of polyethylene glycol (average molecular weight 400) were continuously fed into a paddle dryer heated with a heat medium at 220° C. to mix and heat-treat them to give an absorbent (14). The average residence time in the paddle dryer was 10 minutes. At the exit of the paddle dryer, the absorbent (14) had a temperature of 210° C.

The properties of the absorbent (14) were evaluated in the same way as in Example 1. The results are shown in Table 1.

EXAMPLE 7

One hundred parts of powder B obtained in Example 1 was mixed with 0.5 part of Chemitite PZ-33 [a tradename for 2,2-bishydroxymethylbutanol-tris[3-(1-aziridinyl)propionate] made by Nippon Shokubai Kagaku Kogyo & Co., Ltd.] by a ribbon blender. The mixture was left to stand for 3 days at room temperature (20° to 30° C.) to react them. Thus, an absorbent (15) was obtained.

The properties of the absorbent (15) were evaluated in the same way as in Example 1, and the results are shown in Table 1.

EXAMPLE 8

One hundred parts of powder B obtained in Example 1 was mixed with 0.5 part of ethylene glycol diglycidyl ether in a ribbon blender, and then heat-treated for 30 minutes by raising the heat medium temperature of the ribbon blender to 180° C. An absorbent (16) was obtained. After the heat-treatment, the absorbent (16) had a temperature of 170° C. The results are shown in Table 1.

EXAMPLE 9

One hundred parts of powder B obtained in Example 1 was mixed with 1 part of 2,4-tolylene diisocyanate in a ribbon blender, and left to stand for 3 days at room temperature (20° to 30° C.) to obtain an absorbent (17).

The properties of the absorbent (17) were evaluated in the same way as in Example 1, and the results are shown in Table 1.

EXAMPLE 10

One hundred parts of powder B obtained in Example 1 was mixed with 1 part of triethylenetetraamine by a kneader. Then, the heat medium temperature of the kneader was raised to 200° C., and the mixture was heat-treated for 10 minutes to give an absorbent (18). At the end of the heat-treatment, the absorbent (18) had a temperature of 193° C.

The properties of the absorbent (18) were evaluated in the same way as in Example 1, and the results are shown in Table 1.

COMPARATIVE EXAMPLE 1

The same polymerization as in Example 1 was carried out except that 2 parts of glycerol was added to the aqueous solution of the acrylic acid salt-type monomer. The polymerization product was dried, pulverized and sieved to obtain particles which passed through a 100-mesh sieve (powder G). The powder G was placed on a stainless steel dish, and heat-treated in a hot air dryer at 200° C. for 15 minutes to heat-treat it. Thus, a comparative absorbent (1) was obtained. Upon withdrawal from the dryer, the comparative absorbent (1) had a temperature of 190° C.

The properties of powder G and the comparative absorbent (1) were evaluated in the same way as in Example 1. The results are shown in Table 1.

COMPARATIVE EXAMPLE 2

The gel-like hydrous polymer obtained in Example 1 was cut to cubic pieces with each edge measuring about 3 mm. One hundred parts of the cut cubic piece were mixed well with 0.5 part of glycerol. The mixture was dried, pulverized by a vibratory mill, and sieved on a 100-mesh wire gauze to obtain particles which passed through it (powder H).

Powder H was placed on a stainless dish, and heat-treated in a hot air drier at 200° C. for 15 minutes to obtain a comparative absorbent (2). Upon withdrawal from the dryer, the comparative absorbent (2) had a temperature of 190° C.

The properties of the powder H and the comparative absorbent (2) were evaluated in the same way as in Example 1. The results are shown in Table 1.

TABLE 1

| | | Ratio of absorption | | |
|---|---|---|---|---|
| | | 30 seconds later | 10 minutes later | Formation of fish-eyes (*) |
| Example 1 | Powder A | 41 | 60 | X |
| | Powder B | 31 | 62 | X |
| | Absorbent (1) | 62 | 67 | |
| | Absorbent (2) | 50 | 70 | |
| Example 2 | Absorbent (3) | 60 | 70 | |
| | Absorbent (4) | 61 | 71 | |
| | Absorbent (5) | 59 | 69 | |
| | Absorbent (6) | 60 | 70 | |
| | Absorbent (7) | 59 | 70 | |
| | Absorbent (8) | 62 | 72 | |
| Example 2 | Absorbent (9) | 60 | 70 | |
| | Absorbent (10) | 58 | 72 | |
| Example 3 | Powder C | 25 | 35 | X |
| | Absorbent (11) | 40 | 42 | |
| Example 4 | Powder D | 28 | 48 | X |
| | Absorbent (12) | 43 | 52 | |
| Example 5 | Powder E | 25 | 38 | X |
| | Absorbent (13) | 48 | 60 | |
| Example 6 | Powder F | 23 | 33 | X |
| | Absorbent (14) | 40 | 52 | |
| Example 7 | Absorbent (15) | 48 | 69 | |
| Example 8 | Absorbent (16) | 47 | 67 | |
| Example 9 | Absorbent (17) | 48 | 70 | |
| Example 10 | Absorbent (18) | 47 | 69 | |
| Comparative Example 1 | Powder G | 33 | 45 | X |
| | Comparative absorbent (1) | 35 | 40 | Δ |
| Comparative Example 2 | Powder H | 38 | 58 | X |
| | Comparative absorbent (2) | 42 | 54 | Δ |

(*) The formation of fish-eyes was evaluated as follows:
No fish-eye formed.
ΔFish-eyes did not easily form.
X Fish-eyes formed.

The results shown in Table 1 demonstrate that the absorbents in accordance with this invention do not form fish-eyes, and have a high ratio of absorption and a high speed of absorption. When the polyhydric alcohol was added to an aqueous monomer solution (Comparative Example 1) or when it was added to a gel-like hydrous polymer having a larger particle size than the powder particles (Comparative Example 2), the effect was contrary to that expected, or was small.

What is claimed is:

1. An absorbent article obtained by mixing 100 parts by weight of a powder of an absorbent resin having a carboxyl group selected from the group consisting of hydrolyzate of starch/acrylonitrile graft copolymer; partial neutralization product of starch/acrylic acid graft copolymer; saponification product of vinyl acetate/acrylic ester copolymer; hydrolyzate of acrylonitrile copolymers; hydrolyzate of acrylamide copolymer; crosslinked product of any of the foregoing copolymers; partial neutralization product of polyacrylic acid; and crosslinked partial neutralization product of polyacrylic acid; with 0.001 to 10 parts by weight of a crosslinking agent having at least two functional groups capable of reacting with the carboxyl group per molecule and reacting the absorbent resin powder with the crosslinking agent to crosslink the molecular chains existing at least in the vicinity of the surface of the absorbent resin powder.

2. An absorbent article obtained by mixing 100 parts by weight of a powder of an absorbent resin having a carboxyl group with 0.001 to 10 parts by weight of a crosslinking agent having at least two functional groups capable of reacting with the carboxyl groups per molecule and reacting the absorbent resin powder with the crosslinking agent to crosslink the molecular chains existing at least in the vicinity of the surface of the absorbent resin powder; wherein the absorbent resin having a carboxyl group is an alkali metal acrylate-type polymer obtained by copolymerizing 100 parts by weight of an acrylic acid salt-type monomer composed of 1 to 50 mole% of acrylic acid and 50 to 99 mole% of an alkali metal acrylate and 0 to 5 parts by weight of a crosslinkable monomer in aqueous solution in a monomer concentration of at least 20% by weight, and drying the resulting gel-like hydrous polymer under heat.

3. The absorbent article of claim 1 wherein the absorbent resin powder contains at least 70% by weight of particles which pass through a 60-mesh sieve.

4. The absorbent article of claim 1 wherein the crosslinking agent is a polyhydric alcohol compound.

5. The absorbent article of claim 4 which is obtained by reacting the absorbent resin powder with the polyhydric alcohol compound at 90° to 300° C.

6. The absorbent article of claim 1 wherein the crosslinking agent is a polyglycidyl ether compound.

7. The absorbent article of claim 6 which is obtained by reacting the absorbent resin powder with the polyglycidyl ether compound at 50° to 300° C.

8. The absorbent article of claim 1 wherein the crosslinking agent is a polyfunctional aziridine compound.

9. The absorbent article of claim 8 which is obtained by reacting the absorbent resin powder with the polyfunctional aziridine compound at 10° to 300° C.

10. The absorbent article of claim 1 wherein the crosslinking agent is a polyfunctional amine compound.

11. The absorbent article of claim 10 which is obtained by reacting the absorbent resin powder with the polyfunctional amine compound at 90° to 300° C.

12. The absorbent article of claim 1 wherein the crosslinking agent is a polyfunctional isocyanate compound.

13. The absorbent article of claim 12 which is obtained by reacting the absorbent resin powder with the polyfunctional isocyanate compound at 10° to 300° C.

14. The absorbent article of claim 2 wherein the crosslinking agent is a compound selected from the group consisting of glycerol, polyethylene glycol, triethanolamine, sorbitan monolaurate, polyoxyethylene sorbitan monostearate, trimethylol propane, and sorbitol.

15. The absorbent article of claim 14 wherein the amount of the crosslinking agent is about 0.3 part by weight per 100 parts by weight of the absorbent resin powder.

16. The absorbent article of claim 2 wherein the crosslinking agent is selected from the group consisting of 2,2-bishydroxymethylbutanol-tris[3-(1-aziridinyl)-propionate], ethylene glycol diglycidyl ether, 2,4-tolylene diisocyanate and triethylene tetraamine.

17. The absorbent article of claim 2 wherein the absorbent resin powder is crosslinked with 0.05 part by weight, per 100 parts of the absorbent resin powder of 2,2-bishydroxymethylbutanol-tri[3-(1-aziridinyl)propionate] or ethylene glycol diglycidyl ether.

18. The absorbent article of claim 2 wherein the absorbent resin powder is crosslinked with 1 part by weight, per 100 parts by weight of the absorbent resin powder, of 2,4-tolylene diisocyanate or triethylene tetraamine.

19. An absorbent article which is a reaction product of 100 parts by weight of a powder of an absorbent resin which is a saponified copolymer of vinyl acetate and methylacrylate with 0.001 to 10 parts by weight of a crosslinking agent which is trimethylol propane wherein at least the molecular chains existing at least in the vicinity of the surface of the absorbent resin powder are crosslinked.

20. An absorbent article which is a reaction product of 100 parts by weight of a powder of an absorbent resin which is a crosslinked copolymer of isobutylene and maleic anhydride with 0.001 to 10 parts by weight of a crosslinking agent which is polyethylene glycol wherein at least the molecular chains existing at least in the vicinity of the surface of the absorbent resin powder are crosslinked.

21. The absorbent article of claim 19 wherein 1 part of the crosslinking agent is used per 100 parts of the absorbent resin powder.

22. The absorbent article of claim 20 wherein the crosslinking agent is used in an amount of 0.5 part per 100 parts by weight of the absorbent resin powder.

23. The absorbent article of claim 1 wherein the absorbent resin is obtained by dispersing an aqueous solution of acrylic acid, an alkali metal acrylate containing a water-soluble radical, or mixtures thereof, and containing a water-soluble radical polymerization initiator in a hydrocarbon solvent selected from the group consisting of alicyclic hydrocarbon, aliphatic hydrocarbon, and mixtures thereof, in the presence of a surface-active agent having a hydrophile-lipophile (HLB) balance of 3 to 12, and subjecting the mixture to suspension polymerization.

24. The absorbent article of claim 1 wherein the absorbent resin is a saponification product of a copolymer of a vinyl ester and an ethylenically unsaturated carboxylic acid or derivative thereof.

25. The absorbent article of claim 1 wherein the absorbent resin is a polymer obtained by polymerizing starch, cellulose, or a mixture thereof in an aqueous medium with a monomer having a carboxyl group or a monomer capable of forming a carboxyl group upon hydrolysis and a crosslinking monomer or the hydrolyzate of said polymer.

26. The absorbent article of claim 1 wherein the absorbent resin is the reaction product of an alkaline substance with a maleic anhydride-type copolymer composed of maleic anhydride and at least one monomer selected from the group consisting of alpha-olefins and vinyl compounds or the reaction product thereof with a polyepoxy compound.

* * * * *